(12) United States Patent
Skog

(10) Patent No.: US 6,298,848 B1
(45) Date of Patent: Oct. 9, 2001

(54) DEVICE FOR FLUSHING A DEADSPACE IN MECHANICAL VENTILATION

(75) Inventor: Goran Skog, Bromma (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/413,781

(22) Filed: Oct. 7, 1999

(30) Foreign Application Priority Data

Oct. 27, 1998 (SE) ................................................ 9803685

(51) Int. Cl.⁷ .................................................. A61M 16/00
(52) U.S. Cl. .................................. 128/204.18; 128/205.12
(58) Field of Search ...................... 128/204.18, 204.22, 128/204.23, 204.25, 204.26–204.29, 205.12, 205.13–205.17, 207.15, 207.16, 912, 203.12, 911

(56) References Cited

U.S. PATENT DOCUMENTS

| | | | | |
|---|---|---|---|---|
| 4,197,858 | * | 4/1980 | Osborn | 128/718 |
| 4,617,924 | * | 10/1986 | Heim et al. | 128/204.23 |
| 4,637,386 | * | 1/1987 | Baum | 128/204.21 |
| 5,186,167 | * | 2/1993 | Kolobow | 128/207.14 |
| 5,255,675 | * | 10/1993 | Kolobow | 128/204.18 |
| 5,291,882 | | 3/1994 | Makhoul et al. | |
| 5,400,778 | | 3/1995 | Jonson et al. | |
| 5,507,280 | * | 4/1996 | Henkin et al. | 128/203.12 |
| 5,544,648 | * | 8/1996 | Fischer et al. | 128/207.14 |
| 5,606,968 | * | 3/1997 | Mang | 128/207.14 |
| 5,896,854 | | 4/1999 | Bliss et al. | |
| 5,931,160 | * | 8/1999 | Gilmore et al. | 128/204.21 |
| 5,954,050 | * | 9/1999 | Christopher | 128/204.23 |
| 6,131,571 | * | 10/2000 | Lampotang et al. | 128/204.21 |
| 6,152,133 | * | 11/2000 | Psaros et al. | 128/205.12 |
| 6,196,222 | * | 3/2001 | Heinonen | 128/204.23 |

FOREIGN PATENT DOCUMENTS 0 747 077    12/1996   (EP) .
WO 95/28981  11/1995   (WO) .

* cited by examiner

Primary Examiner—John G. Weiss
Assistant Examiner—Teena Mitchell
(74) Attorney, Agent, or Firm—Schiff Hardin & Waite

(57) ABSTRACT

A device for flushing a deadspace during mechanical ventilation of a patient with a ventilator includes a reservoir having a variable volume container, such as a balloon, adapted to receive and hold a portion of the pressurized breathing gas provided by the ventilator during an inspiration phase and to supply, at least during a final part of an expiration phase, the received breathing gas as pressurized flushing gas to a first end of a conduit which is disposed in a patient's airway. The reservoir has an outlet in pressure communication with the first end of the conduit and operable to supply the flushing gas as a result of the pressure at the first end of the conduit falling below that of the gas within the reservoir.

6 Claims, 2 Drawing Sheets

DEVICE FOR FLUSHING A DEADSPACE IN MECHANICAL VENTILATION

BACKGROUND OF THE INVENTION

1. Field of the Invention

The present invention relates to a device for flushing a deadspace of a mechanically ventilated patient during an expiration phase of artificial ventilation in order to reduce the rebreathing of expired gas.

2. Description of the Prior Art

In the mechanical ventilation of a patient carbon dioxide ($CO_2$) may collect in the patient's airways during an expiration phase of a breathing cycle. The collected $CO_2$ then will be re-breathed during the next inspiration phase of the breathing cycle. It is known that $CO_2$ can be at least partly eliminated from the upper airways by flushing the airways with a flushing gas, preferably a $CO_2$-free flushing gas, during at least a final part of the expiration phase. One known device used to flush the airways in this manner is described in a technical note entitled "Expiratory Flushing of Airways: a Method to Reduce Deadspace Ventilation" by B. Jonson et al (Eur. Respir. J 1990, 3, 1202–1205). This device has a source of pressurized gas, being either a standard gas bottle or a mechanical ventilator (for example of the type ServoVentilator 900C from Siemens-Elema AB, Solna, Sweden). The pressurized gas source supplies breathing gas as the flushing gas after the inspiration phase, and is coupled via a controllable valve system to one end of a conduit. The opposite end of the conduit is insertable into the trachea of the patient so that flushing gas may be supplied into the patient's airway. An electronic control unit' is also provided in operable connection between the mechanical ventilator and the valve system and controls the valve system so that flushing gas, either in pulses or as a continuous stream, is supplied into the conduit during the final part of the expiration phase. Acting on timing information provided to it from the control system of the ventilator, the electronic control unit operates the valve system to supply the flushing gas during a final part of the expiration phase, in this case after 50% of the expiration phase has elapsed and until 10% remains.

This known device has the disadvantages that a specialized flushing source is required, either in the form of a source separate from the mechanical ventilator or in the form of a ventilator that can supply breathing gas even during an expiration phase, and that a relatively complex electronic control system is required to regulate the supply of flushing gas to the patient.

SUMMARY OF THE INVENTION

An object of the present invention is to provide a flushing device in which the aforementioned disadvantages associated with known device are at least alleviated.

The above object is achieved in accordance with the principles of the present invention in a device for flushing a deadspace during mechanical ventilation of a subject with a ventilator which provides pressurized breathing gas to the patient during an inspiration phase of a breathing cycle of the patient, the device having a source of pressurized flushing gas and a conduit with a first end, which is insertable into the patient's airways, and a second end connectable to the source of pressurized flushing gas, and wherein the source of pressurized flushing gas includes a variable-volume reservoir which receives and holds pressurized breathing gas from the ventilator during the inspiration phase and which supplies, at least during a final portion of an expiration phase, the received breathing gas as pressurized flushing gas to the first end of the conduit, dependent on a pressure at the first end of the conduit.

By providing a source of flushing gas in the form of a reservoir which is stocked with pressurized breathing gas supplied by a mechanical ventilator during an inspiration phase, the need is removed for a separate source or for a ventilator adapted as described above in relation to the known flushing device.

Moreover, a relatively simple regulation of flushing gas is achieved by providing an outlet in pressure communication with pressure at the first end of the conduit and operable to supply the flushing gas when a pressure difference across the outlet, due to a reduced pressure at the first end of the outlet as compared to the pressure within the reservoir, reaches or exceeds a predetermined value.

In use, breathing gas supplied through the inlet 25, during an inspiration phase, forces the piston head 23 to move toward the rigid wall 20 and consequently the bias spring 24 is compressed, thereby "storing" pressure from the breathing gas. During the expiration phase the pressure communicated from the patient's airways 4, via the lumen 8 and the line 11, to the outlet 26 reduces compared to that existing during the inspiration phase. When this communicated pressure falls below that pressure "stored" by the spring 24, the piston head 23 moves under the pressure exerted by the compressed spring 24 to force stored breathing gas through the outlet 26 for supply as a pressurized flushing gas.

DESCRIPTION OF THE PREFERRED EMBODIMENTS

Figure 1:
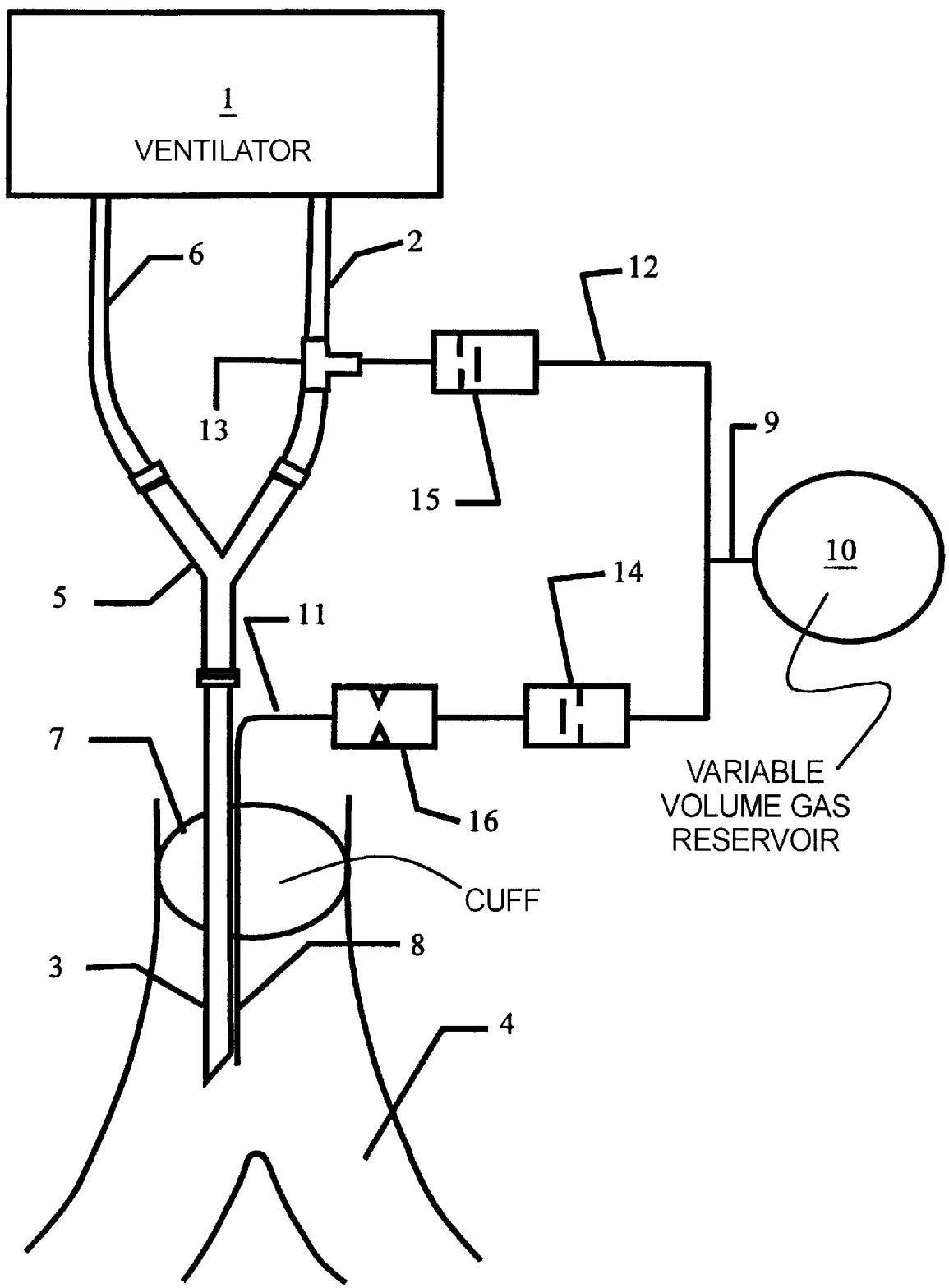
FIG. 1 is a schematic representation of the present invention in use during mechanical ventilation.

Referring to FIG. 1, a mechanical ventilator 1 is connected to an inspiration line 2 to supply a breathing gas at an over-pressure through a tracheal tube 3 and into a patient's airway 4. A Y-piece 5 is provided with one branch connected to the inspiration line 2 and with the tracheal tube 3 connected to a common branch of the conventional Y- piece 5. An expiration line 6 is connected to the other branch of the Y-piece 5 to return expired gas to the ventilator 1. An inflatable cuff 7 is also provided around the tracheal tube 3 to seal the patient's airway 4 against escape of gas other than through the tracheal tube 3. Thus the ventilator 1, lines 2 and 6, Y-piece 5, cuff 7 and tracheal tube 3 are arranged in a manner common in the art of mechanical ventilation to operate in a conventional way.

Also shown in FIG. 1 is a flushing device according to the present invention which has a conduit, here shown as a side lumen 8 integral with the tracheal tube 3, extending to supply a flushing gas at an open end of the tracheal tube 3. Alternatively, the lumen 8 may be independent of, and inserted separately from the tracheal tube 3. The lumen 8 is connected to a common inlet/outlet 9 of a variable volume gas reservoir 10, shown here in the form of a balloon, by a flushing gas supply line 11. A reservoir supply line 12 connects the common inlet/outlet 9 to the inspiration line 2 through a T-piece connector 13, here shown placed in the inspiration line 2 proximate to the Y-piece 5. Optional one-way check-valves 14,15 are shown placed in the supply lines 11,12 respectively to ensure a unidirectional flow path of gas which leads from the inspiration line 2, through the reservoir 10 and out of the lumen 8. A fixed restriction throttle 16 is also provided in this embodiment which acts to regulate the flow of flushing gas out of the reservoir 10 so that the flushing gas can be supplied into the lumen 8 until at least the end of a final part of the expiration phase.

In use, the ventilator 1 is set to supply a pressurized breathing gas through the inspiration line 2 and into the patient's airway 4 during an inspiration phase of a patient's breathing cycle. A portion of this inspiration gas passes, via the T-piece 13, into the reservoir 10 which expands in volume as a result. Since the pressure at the open end of the lumen 8 within the airway 4 is substantially that of the inspiration gas supplied through the tracheal tube 3 that is, substantially that of the flushing gas with the reservoir 10, little or no gas passes from the reservoir 10, and out of the lumen 8 during the inspiration phase. As an expiration phase of the patient's breathing cycle starts a pressure difference develops between outside the open end of the lumen 8 and the flushing gas within the reservoir 10, and the check-valve 14 within the flushing gas supply line 11 opens to allow fresh breathing gas to be supplied into the airway 4 from the reservoir 10, which contracts in volume as a result to thereby maintain a pressurized supply. By adjusting the pressure difference required to open the valve 14, the start of delivery of the flushing gas through the lumen 8 may be delayed until some time after the start of the expiration phase if desired. Additionally or alternatively the size and the elastic properties of the reservoir 10 may be chosen so that a sufficient pressure difference does not develop until some time after the start of the expiration phase.

The flushing gas so supplied from the reservoir 10 displaces expired gas from the point of delivery of the flushing gas (the open end of the lumen 8) toward the ventilator 1. This has the desired effect of reducing the ventilation deadspace in which expired gas will be available for rebreathing by the patient during the next inspiration phase.

Those skilled in the art will readily appreciate from the foregoing description that the flushing device of the present invention represents an essentially passive device which is able to operate without the need of complex control electronics required by prior art devices. Instead, its operation is governed by the gas pressure within the patient's airway 4.

Figure 2:
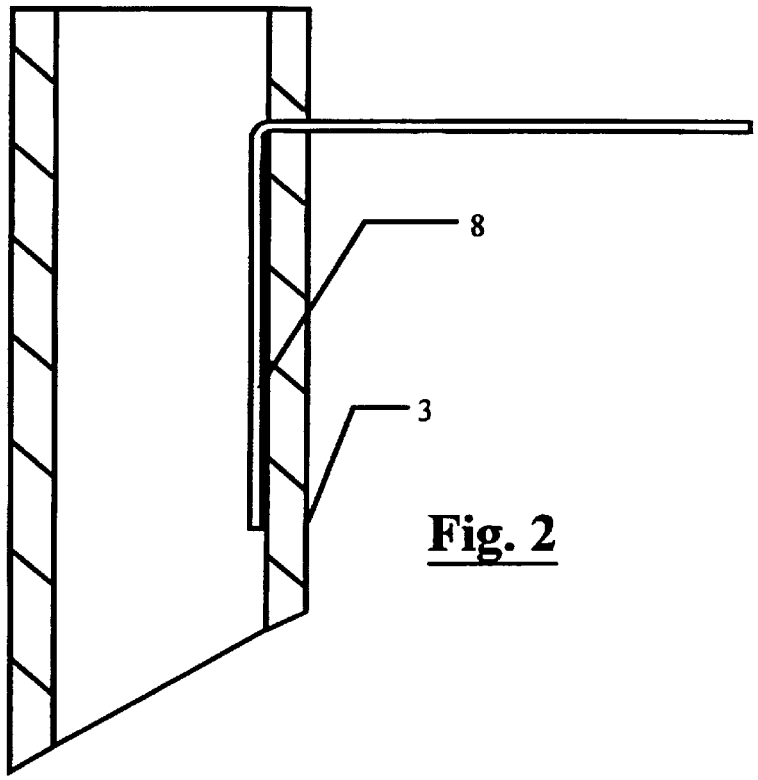
FIG. 2 is a schematic view of a part of an alternative conduit arrangement according to the present invention.

FIG. 2 shows an sectional view of a part of an alternative tracheal tube 3 and lumen 8 arrangement that may be used in the device according to the present invention. In this case the lumen 8 is placed inside the tracheal tube 3 and terminates within the tube 3. In this arrangement mainly expired gas from within the deadspace of the tube 3 is flushed away.

Figure 3:
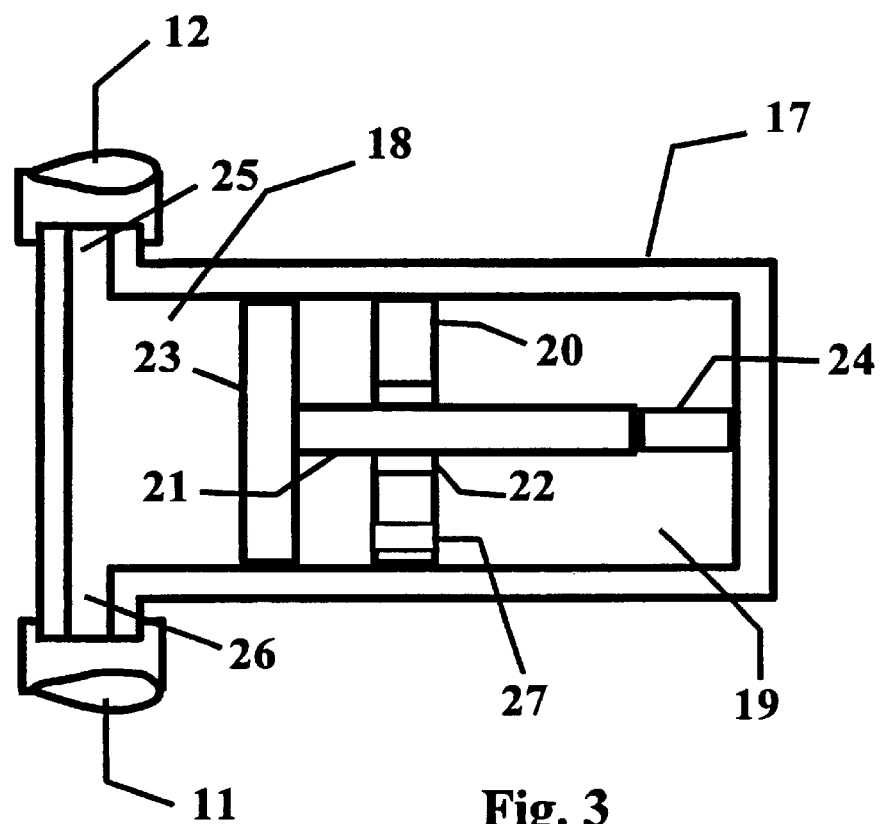
FIG. 3 is a schematic representation of a part of the present invention illustrating an alternative reservoir.

FIG. 3 shows an alternative structure to the balloon for the variable volume reservoir 10. A piston housing 17 is divided into a reservoir compartment 18 and a driving compartment 19 by a rigid support wall 20. A shaft 21 passes through a sealing ring 22 in the wall 20 and is arranged for reciprocal movement between the two compartments 18,19. The shaft 21 terminates with a piston head 23 which is slidable within the reservoir compartment 18 and has an opposite end in contact with a bias spring 24. The reservoir compartment 18 is also provided with an inlet 25, for connection to the pressurized breathing gas supply line 12, and an outlet 26, for connection to the flushing gas supply line 11. A conduit 27 is also provided in the support wall 20 so that gas can move between the two compartments 18,19 as the piston head 23 moves so that it is only the bias spring 24 which will provide any substantial resistance to the movement of the piston head 23 toward the wall 20.

In use, breathing gas supplied through the inlet 25, during an inspiration phase, forces the piston head 23 to move toward the rigid wall 20 and consequently the bias spring 24 is compressed, thereby "storing" pressure from the breathing gas. During the expiration phase the pressure communicated from the patient's airways 4, via the lumen 8 and the line 11, to the outlet 26 reduces compared to that extant during the inspiration phase. When this communicated pressure falls below that pressure "stored" by the spring 24, the piston head 23 moves under the pressure exerted by the compressed spring 24 to force stored breathing gas through the outlet 26 for supply as a pressurized flushing gas.

Other modifications will be apparent to those skilled in the art. For example, the throttle 16 may be made adjustable so as to better match the expiration by different patients or may be controllable to provide pulses of flushing gas; or the reservoir may be provided with a fixed volume.

Although modifications and changes may be suggested by those skilled in the art, it is the intention of the inventor to embody within the patent warranted hereon all changes and modifications as reasonably and properly come within the scope of his contribution to the art.

I claim as my invention:

1. A device for flushing a deadspace during mechanical ventilation of a subject, comprising:
    a ventilator adapted for connection to airways of a patient for providing a pressurized breathing gas during an inspiration phase of a breathing cycle, said inspiration phase being successively followed by an expiration phase;
    a source of pressurized flushing gas;
    a conduit having a first end adapted for insertion into airways of a subject, and a second end connected to said source of pressurized flushing gas; and
    said source of pressurized flushing gas including a reservoir connected to said ventilator to receive and hold pressurized breathing gas from said ventilator during said inspiration phase and to supply, at least during a final part of said expiration phase, the received and held breathing gas as pressurized flushing gas via said second end to said first end of said conduit dependent on pressure at said first end of said conduit.

2. A device as claimed in claim 1 wherein said reservoir has an outlet in pressure communication with said first end of said conduit, said reservoir supplying said pressurized flushing gas through said outlet to said first end of said conduit dependent on a pressure difference between said outlet and said first end of said conduit.

3. A device as claimed in claim 2 further comprising a pressure-operated sealing element connected between said outlet of said reservoir and said first end of said conduit, said pressure-operated sealing element having a first side in pressure communication with said outlet and a second side in pressure communication with said first end of said conduit, and said pressure-operated sealing element normally sealing said outlet and operating to unseal said outlet to supply said pressurized flushing gas to said first end of said conduit dependent on said pressure difference.

4. A device as claimed in claim 1 wherein said reservoir comprises a variable-volume gas container which expands as said pressurized breathing gas is stored therein and which contracts as said pressurized breathing gas is supplied therefrom, as said pressurized flushing gas, to maintain a pressurized supply into said conduit.

5. A device as claimed in claim 4 wherein said variable volume gas container comprises a balloon.

6. A device as claimed in claim 1 further comprising a flow regulator connected between said reservoir and said first end of said conduit for regulating a flow of said pressurized flushing gas from said reservoir to said first end of said conduit.

* * * * *